United States Patent
Boon et al.

(10) Patent No.: US 11,197,840 B2
(45) Date of Patent: Dec. 14, 2021

(54) METHODS OF TREATING OR ALLEVIATING MENTAL DISORDERS AND ASSOCIATED SYMPTOMS

(71) Applicants: The Florey Institute of Neuroscience and Mental Health, Victoria (AU); Deakin University, Victoria (AU)

(72) Inventors: Wah Chin Boon, Victoria (AU); Steve Cheung, Victoria (AU)

(73) Assignee: Wah Chin Boon, North Melbourne (AU)

( * ) Notice: Subject to any disclaimer, the term of this patent is extended or adjusted under 35 U.S.C. 154(b) by 242 days.

(21) Appl. No.: 15/780,913

(22) PCT Filed: Dec. 2, 2016

(86) PCT No.: PCT/IB2016/001853
§ 371 (c)(1),
(2) Date: Jun. 1, 2018

(87) PCT Pub. No.: WO2017/093807
PCT Pub. Date: Jun. 8, 2017

(65) Prior Publication Data
US 2018/0353452 A1 Dec. 13, 2018

(30) Foreign Application Priority Data
Dec. 4, 2015 (AU) ................ 2015905047

(51) Int. Cl.
*A61K 31/201* (2006.01)
*A61P 25/00* (2006.01)

(52) U.S. Cl.
CPC ............ *A61K 31/201* (2013.01); *A61P 25/00* (2018.01)

(58) Field of Classification Search
CPC ............................. A61K 31/201; A61P 25/00
USPC ........................................................ 514/560
See application file for complete search history.

(56) References Cited

FOREIGN PATENT DOCUMENTS

WO     2015172960 A1    11/2015
WO     WO2015/171960 A1 *  11/2015

OTHER PUBLICATIONS

Ito et al. (Evidence Based complementary and Alternative Medicine (2012), pp. 1-6) (Year: 2012).*
Alonso et al. (Neurophychiatric Disease and Treatment (2015), vol. 11 pp. 1939-1955) (Year: 2015).*
DSM-IV [Book] Chapter 300.3; Anxiety Disorder, pp. 417-423. (Year: 1994).*
Genc et al. Journal of Chromatography A (1999), vol. 839, pp. 265-268. (Year: 1999).*
Salem, F. E-Z. H., "Modulatory effects of Trifolium pretense extract and Royal jelly on the function of hypothalamic-pituitary-ovarian axis in ovariectomized rats", International Journal of Pharmacy and Pharmaceutical Sciences, 2013, vol. 5, No. 3, pp. 593-597; p. 595, col. 1, paragaph 1, lines 7-11 and p. 596, col. 1, lines 7-9.
Pyrzanowska, J. et al., "Long-term administration of Greek Royal Jelly improves spatial memory and influences the concentration of brain neurotransmitters in naturally aged Wistar male rats", Journal ofEthnopharmacology, Aug. 8, 2014, (Electronic Publication May 29, 2014),vol. 155, No. 1, pp. 1-8. p. 4, paragraph 3.3.1.
Pyrzanowska, J. etal., "Short-term administration of Greek Royal Jelly changes brain serotonergic transmission in aged rats", Pharmacological Reports, May 2013, vol. 65, Suppl. 1, p. 76; cols. 1 and 2.
Ito, S. et al., "Antidepressant-like activity of 10-hydroxy-trans-2-decenoic Acid, a unique unsaturated Fatty Acid of royal jelly, in stress-inducible depression-like mouse model", Evidence-based complementary and alternative medicine: eCAM, 2012, (Electronic Publication: Jul. 24, 2011), vol. 2012, pp. 1-5; p. 1, Abstract; p. 2, col. 2, para. 2; p. 3, col. 1, paragraphs 1 and 2; and p. 5, 1, 2 and 5-25 col. I, para 2.
WO 20151184509 AI (Deakin University And Florey Institute Of Mental Health ) Dec. 10, 2015; Paragraphs 0002 and 0070.
International Preliminary Report on Patentability dated Mar. 21, 2017, International Application No. PCT/IB2016/001853, all pages.
International Search Report and Written Opinion dated Mar. 21, 2017, International Application No. PCT/IB2016/001853, all pages.
Salem, Modulatory Efeects of Trifolium Pretense Extract and Royal Jelly on the Function of Hypothalamic-Pituitary-Ovarian Axis in Overiectomized Rats, International Journal of Pharmacy and Pharmaceutical Sciences, vol. 5, Issue 3, 2013, 5 pages.
Hill, et al., Estrogen Deficient Male Mice Develop Compulsive Behavior, Biol Psychiatry 2007; 61:359-366, Society of Biological Psychiatry, 8 pages.
Jenck, et al., The Role of 5-HT2C Receptors in Affective Disorders, Ashley Publications Ltd. ISSN: 1354-3784, 1998, 13 pages.

* cited by examiner

*Primary Examiner* — Taina D Matos Negron
(74) *Attorney, Agent, or Firm* — Kilpatrick Townsend & Stockton LLP (57) ABSTRACT

The present invention relates generally to methods for the treatment and/or prophylaxis of mental illness involving administration of 10-HDA. More particularly, methods are taught herein for the treatment and/or prophylaxis of obsessive compulsive disorder, anxiety disorder or a condition characterised by one or more symptoms of a obsessive compulsive disorder or an anxiety disorder.

9 Claims, 5 Drawing Sheets

METHODS OF TREATING OR ALLEVIATING MENTAL DISORDERS AND ASSOCIATED SYMPTOMS

CROSS REFERENCE

This application claims the benefit of Australian Provisional Application No. 2015905047, filed Dec. 4, 2015, which is incorporated by reference herein in its entirety.

TECHNICAL FIELD

The present invention relates generally to methods for the treatment and/or prophylaxis of mental disorders and associated symptoms. In particular, the methods of the present invention are particularly useful in the treatment and/or prophylaxis of obsessive compulsive disorders, anxiety disorders and conditions characterised by one or more symptoms of obsessive compulsive disorders and anxiety disorders.

BACKGROUND OF THE INVENTION

Mental disorders are a broad class of potentially debilitating conditions which can affect people of all ages. Obsessive compulsive disorders and symptoms associated with obsessive compulsive disorders represent a subset of mental disorders characterised by obsessions and/or compulsions, which result in distress and anxiety. Anxiety disorders and symptoms relating to anxiety represent a subset of mental disorders characterised by excessive fear and anxiety. Both obsessive compulsive disorders and anxiety disorders can have significant mental, emotional, physical, and economic consequences for individuals.

Obsessive compulsive disorders (OCD) are a complex group of highly variable mental disorders; distinguished not by a single symptom, but by a multitude of characteristic symptoms. Symptoms typically appear before the age of thirty-five; and more commonly symptoms will appear before the age of twenty, and continue through adulthood. It is estimated that obsessive compulsive and related disorders will affect about 2.3% of people at some point in their life. While males and females are equally affected by OCD and related disorders, male patients often develop OCD at a younger age and general exhibit more severe symptoms. Furthermore, it has been reported that female OCD patients exhibit worse symptoms during menstruation, post-menopause or and/or within one month of childbirth, suggesting some degree of hormonal influence.

Current treatments for obsessive compulsive disorders aim to increase quality of life and functional independence as well as reduce associated deficits and family distress. Typical treatment involves the use of educational or behavioural therapies. Outside of behavioural therapies, a number of different medications have been used, with varying degrees of success. Selective serotonin reuptake inhibitors (SSRIs) may be used in conjunction with behavioural therapy to alleviate symptoms. However, 40-60% of OCD-patients fail to respond to SSRI-monotherapy. Furthermore, atypical antipsychotics and dopamine antagonists have also been found to be useful, when used in addition to an SSRI, in treatment-resistant cases. However, OCD patients often respond atypically to medications or the prescribed medications may have other adverse side effects. In the absence of treatment, the course of an obsessive compulsive disorder is usually chronic, however the nature and severity of symptoms may vary over time and/or in response to environmental triggers and cues.

Anxiety disorders and symptoms relating to anxiety in accordance with the present invention may include, for example disorders that share features of excessive fear and anxiety and related behavioural disturbances. The emotions present in anxiety disorders range from simple nervousness to bouts of terror. Most anxiety disorders occur more frequently in females than in males (approximately 2:1 ratio). Symptoms may appear at any time, though for many patients, symptoms often appear in childhood. Treatment depends on the nature and severity of symptoms. However, treatment of anxiety disorders typical involves the use of educational or behavioural therapy, in conjunction with a number of different medications, such as antidepressants and anti-psychotics, including selective serotonin reuptake inhibitors (SSRIs). Medication is often associated with adverse side effects. In the absence of treatment, many anxiety disorders persist as chronic conditions.

Accordingly, there is an on-going need to develop new therapeutic agents or methods of treating and/or preventing mental disorders and associated symptoms such as OCD and anxiety disorders.

SUMMARY OF THE INVENTION

The applicants of the present application have surprisingly found that 10-hydroxy-2-decenoic acid (10-HDA), compositions containing 10-HDA, and pharmaceutically acceptable salts thereof, offer an effective therapy for the treatment and/or prophylaxis of mental disorders, in particular, obsessive compulsive disorders and anxiety disorders.

10-HDA, also referred to as queen bee acid, is a fatty acid and key component of royal jelly; a honey bee secretion used in the nutrition of larvae and adult queens. In view of the alkene functional group, it is recognised that 10-HDA may exist as either the trans or cis geometric isomers. These isomers may also be referred to as (E) or (Z) isomers, respectively.

Trans or (E)-10-hydroxy-2-decenoic acid has the following structure:

Cis or (Z)-10-hydroxy-2-decenoic acid has the following structure:

Throughout this specification reference to 10-HDA is intended to mean reference to each of the (E) isomer and (Z) isomer, as well as mixtures of the two isomers, unless otherwise specified.

In one aspect of the invention, there is provided a method for the treatment and/or prophylaxis of a mental disorder, comprising administering to a mammal in need thereof an effective amount of 10-hydroxy-2-decenoic acid or a pharmaceutically acceptable salt thereof, wherein the mental disorder is selected from an obsessive compulsive disorder, an anxiety disorder or a condition characterised by one or more of symptoms of obsessive compulsive disorder or an anxiety disorder.

In one or more embodiments, the method of the present invention comprises administering an effective amount of trans 10-hydroxy-2-decenoic acid or a pharmaceutically acceptable salt thereof.

In still other embodiments, the method of the present invention comprises administering an effective amount of cis 10-hydroxy-2-decenoic acid or a pharmaceutically acceptable salt thereof.

In further embodiments, the method of the present invention comprises administering an effective amount of a mixture of trans and cis 10-hydroxy-2-decenoic acid or a pharmaceutically acceptable salt thereof.

In one aspect of the invention, there is provided a method for the treatment and/or prophylaxis of a mental disorder, comprising administering to a mammal in need thereof a pharmaceutical composition comprising 10-hydroxy-2-decenoic acid, or a pharmaceutically acceptable salt thereof, wherein the mental disorder is selected from an obsessive compulsive disorder, an anxiety disorder or a condition characterised by one or more of symptoms of obsessive compulsive disorder or an anxiety disorder.

In one or more embodiments, the method of the present invention comprises administering a pharmaceutical composition comprising trans 10-hydroxy-2-decenoic acid, or a pharmaceutically acceptable salt thereof. In one or more embodiments, the method of the present invention comprises administering a pharmaceutical composition comprising cis 10-hydroxy-2-decenoic acid, or a pharmaceutically acceptable salt thereof. In one or more embodiments, the method of the present invention comprises administering a pharmaceutical composition comprising a mixture of cis and trans 10-hydroxy-2-decenoic acid, or a pharmaceutically acceptable salt thereof. In one or more embodiments, the method of the present invention comprises administering a pharmaceutical composition comprising trans 10-hydroxy-2-decenoic acid, or a pharmaceutically acceptable salt thereof, wherein the trans 10-hydroxy-2-decenoic acid is synthetic trans 10-hydroxy-2-decenoic acid.

In one or more embodiments, the mental disorder may be an obsessive compulsive disorder, in particular an obsessive compulsive disorder selected from the group consisting of obsessive-compulsive disorder (OCD), body dysmorphic disorder, hoarding disorder, trichotillomania (hair-pulling disorder), excoriation (skin picking) disorder, substance/medication-induced obsessive-compulsive and related disorder, obsessive-compulsive and related disorder due to another medical condition, and other specified obsessive-compulsive and related disorder and unspecified obsessive-compulsive and related disorder (e.g., body-focused repetitive behaviour disorder, obsessional jealousy).

In other embodiments, the mental disorder may be an anxiety disorder, in particular, an anxiety disorder selected from the group consisting of separation anxiety disorder, selective mutism, phobias, social anxiety disorder (social phobia), panic disorder, panic attack specifier, agoraphobia, generalized anxiety disorder, substance/medication-induced anxiety disorder, anxiety disorder due to another medical condition, other specified anxiety disorder, unspecified anxiety disorder.

In other aspects, 10-hydroxy-2-decenoic acid or a pharmaceutically acceptable salt thereof in accordance with the present invention may be administered as a composition. In some embodiments, the composition may comprise royal jelly, an extract of royal jelly, or a composition derived from royal jelly. In other embodiments, the composition is not royal jelly, an extract of royal jelly, nor a composition derived from royal jelly. In other embodiments, the 10-hydroxy-2-decenoic acid, or a pharmaceutically acceptable salt thereof, is synthetic 10-hydroxy-2-decenoic acid. In some embodiments, the 10-hydroxy-2-decenoic acid, or a pharmaceutically acceptable salt thereof, in accordance with the present invention, is administered as a composition consisting of 10-hydroxy-2-decenoic acid and at least one pharmaceutically acceptable excipient. In some embodiments, the 10-hydroxy-2-decenoic acid, or a pharmaceutically acceptable salt thereof, in accordance with the present invention, is administered as a composition consisting of trans 10-hydroxy-2-decenoic acid and at least one pharmaceutically acceptable excipient. In some embodiments, the 10-hydroxy-2-decenoic acid, or a pharmaceutically acceptable salt thereof, in accordance with the present invention, is administered as a composition consisting of cis 10-hydroxy-2-decenoic acid and at least one pharmaceutically acceptable excipient. In some embodiments, the 10-hydroxy-2-decenoic acid, or a pharmaceutically acceptable salt thereof, in accordance with the present invention, is administered as a composition consisting of a mixture of trans and cis 10-hydroxy-2-decenoic acid and at least one pharmaceutically acceptable excipient.

In still other aspects, the present invention provides the use of 10-hydroxy-2-decenoic acid or a pharmaceutically acceptable salt thereof in the preparation of a medicament for the treatment and/or prophylaxis of mental disorders, wherein the mental disorder is selected from an obsessive compulsive disorder, an anxiety disorder or a condition characterised by one or more of symptoms of obsessive compulsive disorder or an anxiety disorder.

Unless defined otherwise, all technical and scientific terms used herein have the same meanings as commonly understood by one of ordinary skill in the art to which this invention belongs.

The reference to any prior art in this specification is not, and should not be taken as, an acknowledgment or any form of suggestion that that prior art forms part of the common general knowledge.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Provided herein is a method for treatment and/or prophylaxis of a mental disorder, comprising administering to a mammal in need thereof an effective amount of 10-hydroxy-2-decenoic acid (10-HDA) or a pharmaceutically acceptable salt thereof.

As highlighted above, in view of the alkene functional group, it is recognised that 10-HDA may exist as either the trans or cis isomers, or mixtures thereof. Accordingly, in some embodiments, the methods and uses described herein comprise administering an effective amount of trans 10-hydroxy-2-decenoic acid or a pharmaceutically acceptable salt thereof. In still other embodiments, the methods and uses described herein comprise administering an effective amount of cis 10-hydroxy-2-decenoic acid or a pharmaceutically acceptable salt thereof. In further embodiments, the methods and uses described herein comprise administering an effective amount of a mixture of 10-hydroxy-2-decenoic acid or pharmaceutically acceptable salts thereof.

In some embodiments the 10-hydroxy-2-decenoic acid is synthetic 10-hydroxy-2-decenoic acid.

In some embodiments the 10-hydroxy-2-decenoic acid is purified 10-hydroxy-2-decenoic acid.

In some embodiments the 10-hydroxy-2-decenoic acid is isolated and purified 10-hydroxy-2-decenoic acid.

In some embodiments the 10-hydroxy-2-decenoic acid is not derived from royal jelly.

In some embodiments the 10-hydroxy-2-decenoic acid is administered as a pharmaceutical composition. In some embodiments the pharmaceutical composition comprises at least one pharmaceutically acceptable excipient. In some embodiments the pharmaceutical composition comprises 10-hydroxy-2-decenoic acid and at least one pharmaceutically acceptable excipient. In some embodiments the pharmaceutical composition consists of 10-hydroxy-2-decenoic acid and at least one pharmaceutically acceptable excipient. In some embodiments the pharmaceutical composition consists of 10-hydroxy-2-decenoic acid as the active ingredient, and at least one pharmaceutically acceptable excipient. In some embodiments the pharmaceutical composition does not provoke an immunogenic response.

The methods described herein advantageously provide a reduction of core symptoms of mental disorders, in particular the symptoms associated with a mental disorder such as an obsessive compulsive disorder or an anxiety disorder. In some aspects, the methods of the present invention advantageously provide a reduction in the severity of symptoms of OCD, for example, repetitive behaviours.

In some embodiments, the person is currently in need of such treatment as determined by a qualified physician. In other embodiments, the compound is administered in a prophylactic sense.

References to a "mental disorder" or a "mental illness", are used interchangeably, and should be understood as a reference to a condition characterised by behavioural, cognitive and/or emotional patterns or disturbances which influence or reduce an individual's capacity to function in ordinary life.

In one embodiment, said mental disorder is a condition which is characterised by one or more symptoms of an obsessive compulsive disorder or an anxiety disorder, including obsessive compulsive disorder or generalised anxiety disorder.

The term obsessive compulsive disorders (OCDs), as used herein, would be clear to persons skilled in the art and includes obsessive-compulsive disorder (OCD), body dysmorphic disorder, hoarding disorder, trichotillomania (hair-pulling disorder), excoriation (skin-picking) disorder, substance/medication-induced obsessive-compulsive and related disorder, obsessive-compulsive and related disorder due to another medical condition, and other specified obsessive-compulsive and related disorder and unspecified obsessive-compulsive and related disorder (e.g., body-focused repetitive behaviour disorder, obsessional jealousy), as defined in the Diagnostic and Statistical Manual of Mental Disorders 5 (DSM-5) published in May 2013. The Diagnostic and Statistical Manual of Mental Disorders 5 outlines diagnose of OCD by the presence of obsessions, compulsions, or both. Furthermore, the obsessions or compulsions are time-consuming (e.g., take more than 1 hour per day) or cause clinically significant distress or impairment in social, occupational, or other important areas of functioning.

The Diagnostic and Statistical Manual of Mental Disorders 5 outlines that obsessions are defined by:
1. Recurrent and persistent thoughts, urges, or images that are experienced, at some time during the disturbance, as intrusive and unwanted, and that in most individuals cause marked anxiety or distress.
2. The individual attempts to ignore or suppress such thoughts, urges, or images, or to neutralize them with some other thought or action (i.e., by performing a compulsion).

Furthermore, the Diagnostic and Statistical Manual of Mental Disorders 5 outlines that compulsions are defined by:
1. Repetitive behaviours (e.g., hand washing, ordering, checking) or mental acts (e.g., praying, counting, repeating words silently) that the individual feels driven to perform in response to an obsession or according to rules that must be applied rigidly.
2. The behaviours or mental acts are aimed at preventing or reducing anxiety or distress, or preventing some dreaded event or situation; however, these behaviours or mental acts are not connected in a realistic way with what they are designed to neutralize or prevent, or are clearly excessive.

Reference to "symptoms characteristic of OCD" should be understood as a reference to any one or more symptoms which may occur in an individual suffering from OCD. These symptoms may be evident throughout the course of the disorder or they may be evident only transiently or periodically. For example, an individual may exhibit severe repetitive behaviours (e.g., washing, checking) in response to specific environmental cues or stressors. It should also be understood that the subject symptoms may not necessarily be exhibited by all individuals suffering from OCD. For example, some individuals may suffer from obsessions only, such as persistent thoughts or urges in the absence of compulsions, such as repetitive behaviours. However, for the purpose of the present invention, any such symptoms, irrespective of how many or few OCD patients ever actually exhibit the given symptom, are encompassed by this definition.

Obsessions are typically repetitive and persistent thoughts, images, or urges. Compulsions or rituals are repetitive behaviours or mental acts that the individual feels driven to perform in response to an obsession or according to rules that must be applied rigidly. Where compulsions involve repetitive motions or behaviours, these may include actions which may be repeated over and over again. For example, an OCD patient with repetitive and persistent thoughts of contamination (i.e. an obsession), might spend a lot of time cleaning (i.e. a compulsion).

Obsessions are not pleasurable or voluntary, but cause marked distress or anxiety in most individuals. Similarly, Compulsions are not done for pleasure, although some individuals experience relief from anxiety or distress.

Obsessions and compulsions associated with OCD are typically time-consuming or cause clinically significant distress or impairment. It will be appreciated that the nature, frequency and severity of obsessions and compulsions varies between individuals (e.g., some have mild to moderate symptoms i.e. 1-3 hours per day; others have nearly constant intrusive thoughts or compulsions). Typical examples of obsessions and compulsions common to OCD include, but are not limited to:

cleaning (contamination obsessions and cleaning compulsions);
symmetry (symmetry obsessions and repeating, ordering, and counting compulsions);
forbidden or taboo thoughts (e.g., aggressive, sexual, or religious obsessions and related compulsions); and
harm (e.g., fears of harm to oneself or others and checking compulsions);
dysfunctional beliefs (e.g., inflated sense of responsibility, tendency to overestimate threat; perfectionism and intolerance of uncertainty; and/or over-importance of thoughts).

People with OCD often thrive on routine. A change in the normal pattern of the day can cause severe anxiety and/or distress for an individual suffering from OCD. They might "lose control" and have a "melt down" or tantrum, especially in response to environment triggers or where the performance of a particular compulsion is interrupted. Furthermore, an individual suffering from OCD may develop routines that could be perceived as unusual or unnecessary. For example, an individual suffering from OCD may be convinced that the house will burn down if the stove is not checked 30 times. Deviation from these types of routines may cause severe anxiety and distress.

The term "anxiety disorders", as used herein, would be clear to persons skilled in the art and includes disorders that share features of excessive fear and anxiety and related behavioural disturbances. For example, anxiety disorders may include separation anxiety disorder, selective mutism, specific phobia, social anxiety disorder (social phobia), panic disorder, panic attack specifier, agoraphobia generalized anxiety disorder, substance/medication-induced anxiety disorder, anxiety disorder due to another medical condition, other specified anxiety disorder, and/or unspecified anxiety disorder as defined in the Diagnostic and Statistical Manual of Mental Disorders 5 (DSM-5) published in May 2013.

Anxiety disorders share similar symptoms, but differ from one another in the types of objects or situations that induce fear, anxiety, or avoidance behaviour, and the associated cognitive ideation. Fear is recognised as the emotional response to real or perceived imminent threat. Anxiety is recognised as anticipation of future threat. Overlap between the two states may exist in individuals suffering from anxiety disorders. It is generally recognised that anxiety disorders differ from developmentally normative fear or anxiety by being excessive or persisting beyond developmentally appropriate periods. They differ from transient fear or anxiety, often stress-induced, by being persistent.

Examples of anxiety disorders include generalized anxiety disorder. The Diagnostic and Statistical Manual of Mental Disorders 5 outlines that generalized anxiety disorder is defined by:

excessive anxiety and worry (apprehensive expectation), occurring more days than not for at least 6 months, about a number of events or activities (such as work or school performance);
individual finds it difficult to control the worry;
anxiety and worry may be associated with one or more of:
  a. Restlessness or feeling keyed up or on edge,
  b. Being easily fatigued,
  c. Difficulty concentrating or mind going blank,
  d. Irritability,
  e. Muscle tension, and
  f. Sleep disturbance (difficulty falling or staying asleep, or restless, unsatisfying sleep or insomnia).
clinically significant distress or impairment in social, occupational, or other important areas of functioning.

Reference to "symptoms characteristic of anxiety disorders" should be understood as a reference to any one or more symptoms which may occur in an individual suffering from an anxiety disorder. These symptoms may be evident throughout the course of the disorder or they may be evident only transiently or periodically. For example, an individual may exhibit severe sleep disturbance (e.g., insomnia) in response to specific environmental cues or stressors. It should also be understood that the subject symptoms may not necessarily be exhibited by all individuals suffering from anxiety disorder. For example, some individuals may rely on avoidance behaviours which may mask underlying symptoms of anxiety and fear. However, for the purpose of the present invention, any such symptoms, irrespective of how many or few anxiety disorder patients ever actually exhibit the given symptom, are encompassed by this definition.

In addition to the fact that there may be significant variation between patients suffering from mental disorders, such as anxiety disorders or anxiety disorders, in terms of which symptoms they exhibit, it should also be understood that there are other mental disorders which are also characterised by one or more of these symptoms. The obsessions and compulsions exhibited by OCD patients, for example, may also commonly be observed in patients with anxiety disorders; major depressive disorders; other obsessive-compulsive and related disorders, such as body dysmorphic disorder, hoarding disorder, trichotillomania (hair-pulling disorder); eating disorders; tics; psychotic disorders, such as delusional disorder; compulsive-like behaviours; and/or obsessive-compulsive personality disorder. The fear and anxiety exhibited by anxiety disorder patients may be observed in patients with obsessive compulsive disorders, post-traumatic stress disorder and adjustment disorders, major depressive disorders, bipolar disorder, other psychotic disorders, social anxiety disorder, substance or medication induced anxiety disorder. Accordingly, reference to a condition characterised by one or more symptoms characteristic of OCD and/or anxiety disorders should be understood as a reference to any mental disorder which is characterised by the presence of one or more of these symptoms.

Without wishing to be bound by theory, the present invention is predicated in part on the inventors' observation that an Aromatase Knockout mouse (ArKO) model may exhibit behavioural phenotypes reflective of some of the key diagnostic behaviours and symptoms of OCD disorder. In particular, the inventors have demonstrated that the lack of a normal functioning aromatase will precipitate OCD-like repetitive behavioural disturbances in a male Aromatase Knockout mouse (ArKO) mouse (Hill et al. (2007) *Biol. Psychiatry*; vol. 61 pp. 359-366, incorporated herein by reference).

Still other behavioural phenotypes exhibited by the male ArKO mouse may be reflective of some of the key diagnostic behaviours and symptoms of anxiety disorders.

For example, some key behavioural disturbances observed in male Aromatase Knockout mice (ArKO) which are reflective of one or more symptoms of OCD and anxiety disorders include, but are not limited to, compulsive wheel running, compulsive grooming, vocalisation deficit, and/or social interaction deficit. These and other behavioural disturbances are considered to be substantially similar to obsessions and compulsions exhibited by human patients suffering from OCD, and furthermore, may be indicative of anxiety and/or fear exhibited by human patients suffering from anxiety disorders.

The inventors have surprisingly found that the administration of 10-HDA to male ArKO mice alleviated one or more of the behavioural disturbances, including a reduction in wheel running and/or compulsive grooming.

Accordingly, in one aspect, the present invention provides a method treating or alleviating a mental disorder.

In particular, in some embodiments, the present invention provides a method of treating or alleviating an obsessive compulsive disorder, an anxiety disorder or a condition characterised by one or more symptoms of obsessive compulsive disorder or an anxiety disorder.

Serotonin (5-hydroxytryptamine) receptor 2C (HTR2C) is a member of the serotonin receptor family of G-protein coupled receptors. HTR2C expression and activity has been shown to be modulated through RNA editing. J. Cheng et al. (2015) ChemMedChem 10(12): 1963-1967; K. Iwamoto et al. (2009) RNA Biology 6(3): 248-253. HTR2C is primarily expressed in the central nervous system (CNS) and has been implicated in several CNS disorders. J. Cheng et al. (2015) ChemMedChem 10(12): 1963-1967. For example, modulators of HTR2C have been shown to have therapeutic potential for schizophrenia, obesity, addiction, obsessive compulsive disorder, and depression. J. Cheng et al. (2015) ChemMedChem 10(12): 1963-1967; A. Frisch et al. (2000) Eur Neuropsychopharmacol 10(3): 205-209; F. Jenck et al. (1998) Expert Opin Investig Drugs 7(10): 1587-1599. The role of HTR2C in the CNS has also been demonstrated using HTR2C knockout mice. These mice exhibit behaviours such as over-eating, hyperexcitability, compulsive behaviour, and epileptic convulsions. J. M. Chou-Green et al. (2003) Physiol Behavior 78(4-5): 641-649; M. Tohda et al. (2006) J Pharmacol Sci 100: 427-432.

Dynamin-3 (DNM3) is a member of the dynamin family of GTPases that are primarily involved in membrane fission events. DNM3 is highly expressed in the CNS, being specifically enriched in the brain. B. Calabrese et al. (2015) Mol Cell Neurosci 68: 36-45; A. Romeu et al. (2014) BMC Research Notes 7: 188. Within the CNS, DNM3 plays a role in synaptic vesicle recycling and is found in post-synaptic densities. B. Calabrese et al. (2015) Mol Cell Neurosci 68: 36-45; A. M. Gonzalez-Jamett et al. (2014) Journal of Neurochemistry 128: 210-223. Genome wide association studies have implicated DNM3 as being linked to CNS disorders such as obsessive compulsive disorder. J. Costas et al. (2016) Transl Psychiatry 6: e768.

Provided herein is a method of modulating dynamin 3 expression comprising contacting cortical neurons with 10-hydroxy-2-decenoic acid.

Provided herein is a method of modulating dynamin 3 expression in a subject comprising administering to the subject a pharmaceutical composition comprising 10-hydroxy-2-decenoic acid, or a pharmaceutically acceptable salt thereof.

Provided herein is a method of modulating 5-hydroxytryptamine receptor 2C expression comprising contacting cortical neurons with 10-hydroxy-2-decenoic acid.

Provided herein is a method of modulating 5-hydroxytryptamine receptor 2C expression in a subject comprising administering to the subject a pharmaceutical composition comprising 10-hydroxy-2-decenoic acid, or a pharmaceutically acceptable salt thereof.

Provided herein is a method of modulating both dynamin 3 expression and 5-hydroxytryptamine receptor 2C expression comprising contacting cortical neurons with 10-hydroxy-2-decenoic acid.

Provided herein is a method of modulating both dynamin 3 expression and 5-hydroxytryptamine receptor 2C expression in a subject comprising administering to the subject a pharmaceutical composition comprising 10-hydroxy-2-decenoic acid, or a pharmaceutically acceptable salt thereof.

The term "mammal" as used herein includes humans, primates, livestock animals (e.g. horses, cattle, sheep, pigs, donkeys), laboratory test animals (e.g. mice, rats, guinea pigs), companion animals (e.g. dogs, cats) and captive wild animals (e.g. kangaroos, deer, foxes). Preferably, the mammal is a human.

For certain of the abovementioned conditions it is clear that the methods of the invention may be used prophylactically as well as for the alleviation of acute symptoms. Accordingly, references herein to "treatment" or the like are to be understood to include such prophylactic treatment, as well as treatment of acute conditions.

The term "indicative", as used herein, denotes an association or affiliation of a subject closely to a group or population of subjects who present, or likely to present, with the same or a similar clinical manifestations or response to the treatment. For example, the clinical manifestations of OCD are encompassed by symptoms of OCD. Furthermore, the clinical manifestations of anxiety disorder are encompassed by symptoms of anxiety disorders.

One of skill in the art will be familiar with the difficulties in administering traditional antipsychotic and antidepressant medications; including lag phases and heightened anxiety in the initial stages of treatment before the antidepressant effects are seen. Thus, in certain embodiments, it is envisaged that 10-HDA, pharmaceutically acceptable salts thereof or compositions comprising 10-HDA as described herein may be administered to a person in need thereof as a substitute or replacement for traditional medication. In other embodiments, it is envisaged that 10-HDA, pharmaceutically acceptable salts thereof or compositions comprising 10-HDA may be administered to a subject in need thereof as a supplement or adjunct to traditional medication. In still other embodiments, it is envisaged that 10-HDA, or compositions comprising 10-HDA, or a pharmaceutically acceptable salts thereof, may be administered to a person in need thereof in the absence of adjunct therapy. In still other embodiments, it is envisaged that 10-HDA, compositions comprising 10-HDA, or pharmaceutically acceptable salts thereof, may be administered to a person in need thereof in conjunction with, or as an adjunct to, behavioural or cognitive therapies.

Replacing traditional medication with 10-HDA, compositions comprising 10-HDA, or pharmaceutically acceptable salts thereof, may be advantageous, particularly where the traditional medication is associated with one or more adverse effects (e.g., sleepiness, tremors, anxiety, suicidal ideation, etc.). Examples of medication would be known to those skilled in the art and include, but are not limited to, selective serotonin re-uptake inhibitors (SSRI), antipsychotics, antidepressants, lithium and other mood stabilisers.

In other embodiments, 10-HDA, compositions comprising 10-HDA, or pharmaceutically acceptable salts thereof are administered to a subject in need thereof, together with traditional medication for a discrete period of time, to address symptoms such repetitive behaviours and/or anxiety, with the option of discontinuing treatment with the 10-HDA whilst continuing with the traditional therapy. In still other embodiments, the person in need thereof may be treated with 10-HDA, compositions comprising 10-HDA, or pharmaceutically acceptable salts thereof and one or more traditional medications (administered sequentially or in combination) for the duration of the treatment period. Such combination therapy may be particularly useful, for example, where an additive or synergistic therapeutic effect is desired.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of condition, or the amelioration of one or more symptoms (e.g., one or more discernible symptoms) of said condition (i.e., "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of a condition described herein. In other embodiments the terms "treat", "treatment" and "treating" refer to the inhibition of the progression of a condition described herein, either physically by, e.g., stabilization of a discernible symptom or physiologically by, e.g., stabilization of a physical parameter, or both.

The desired therapeutic activity, or effect, will typically depend on the condition being treated. For example, where the subject is being treated for obsessive compulsive disorder, the therapeutic effect may be a reduction in at least one clinical symptom of obsessive compulsive disorder, including, but not limited to repetitive behavioural disturbances. In the case where the subject is being treated for anxiety disorder, the therapeutic effect may be a reduction in at least one clinical symptom of the anxiety disorder, including, but not limited to, reduction in anxiety or a reduction in sleep disturbance (i.e. improved sleep patterns).

The terms "preventing" and "prophylaxis" as used herein refer to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. As used in a standard text in the field, the Physician's Desk Reference, the terms "prevent", "preventing" and "prevention" with regard to a disorder or disease, refer to averting the cause, effects, symptoms or progression of a disease or disorder prior to the disease or disorder fully manifesting itself.

The compounds of the present invention are administered to the person in need thereof in a treatment effective amount. In some embodiments, a treatment effective amount is a therapeutically effective amount or a prophylactically effective amount. The term "therapeutically effective amount" as used herein means that amount of an active compound that elicits the biological or medicinal response in a tissue, system, animal or human that is being sought by a researcher, veterinarian, medical doctor, or other clinician. The therapeutically effective amount of the compound to be administered will be governed by such considerations, and is the minimum amount necessary to ameliorate, cure, or treat the disease or disorder or one or more of its symptoms. The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease or symptom) and secondary prophylaxis (whereby the disease or symptom has already developed and the patient is protected against worsening of this process).

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 100 g per kg of body weight per dosage. The dosage may be in the range of 1 µg to 10 g per kg of body weight per dosage, such as is in the range of 1 mg to 1000 mg per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 200 mg per kg of body weight per dosage, such as up to 50 mg per body weight per dosage.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

In certain embodiments, an effective amount of a compound for administration one or more times a day to a 70 kg adult human may comprise about 0.0001 mg to about 4000 mg, about 0.0001 mg to about 3000 mg, about 0.0001 mg to about 200 mg, about 0.001 mg to about 1500 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of compound per unit dosage form.

In certain embodiments, the extracts and/or compounds of the invention may be at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, and from about 1 mg/kg to about 25 mg/kg, of subject body weight per day, one or more times a day, to obtain the desired therapeutic effect.

Suitable dosage amounts and dosing regimens can be determined by the attending physician and may depend on the particular condition being treated, the severity of the condition as well as the general age, health and weight of the subject. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Compounds of the present invention may be administered in a single dose or a series of doses. While it is possible for the compound to be administered alone, in some embodiments it may be preferable to present it as a composition, preferably as a pharmaceutical composition. The formulation of such compositions is well known to those skilled in the art. Such a composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents.

The compounds and associated pharmaceutical compositions of the present invention may be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another antipsychotic, anticonvulsant or antidepressant medication, an "effective amount" of the second agent will depend on the type of drug used. Suitable dosages are known for approved agents and can be adjusted by a person skilled in the art according to the condition of the subject, the type of condition(s) being treated and the amount of a compound, extract or composition being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

The phrase "combination therapy" as used herein, is understood to refer to administration of an effective amount, using a first amount of 10-HDA, a composition comprising 10-HDA or a pharmaceutically acceptable salt thereof as described herein, and a second amount of an additional suitable therapeutic agent.

In certain embodiments, 10-HDA, or a composition comprising 10-HDA as described herein, or a pharmaceutically acceptable salt thereof, and the additional therapeutic agent, are each administered in an effective amount (i.e., each in an amount which would be therapeutically effective if administered alone). In other embodiments, 10-HDA, or a composition comprising 10-HDA as described herein, or a pharmaceutically acceptable salt thereof, and the additional therapeutic agent are each administered in an amount which alone does not provide a therapeutic effect (a sub-therapeutic dose). In yet other embodiments, 10-HDA, or a composition comprising 10-HDA as described herein, or a pharmaceutically acceptable salt thereof, can be administered in an effective amount, while the additional therapeutic agent is administered in a sub-therapeutic dose. In still other embodiments, 10-HDA, or a composition comprising 10-HDA as described herein, or a pharmaceutically acceptable salt thereof, can be administered in a sub-therapeutic dose, while the additional therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a person in need thereof.

Co-administration encompasses administration of the first and second amounts of therapeutic compounds in an essentially simultaneous manner, such as in a single pharmaceutical composition, for example, capsule or tablet having a fixed ratio of first and second amounts, or in multiple, separate capsules or tablets for each. In addition, such co-administration also encompasses use of each compound in a sequential manner in either order. When co-administration involves the separate administration of the first amount of 10-HDA, or a composition comprising 10-HDA, as described herein, or a pharmaceutically acceptable salt thereof, and a second amount of an additional therapeutic agent, they are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life, and kinetic profile. For example, 10-HDA, or a composition comprising 10-HDA as described herein, or a pharmaceutically acceptable salt thereof, and the second therapeutic agent can be administered in any order within about 24 hours of each other, within about 16 hours of each other, within about 8 hours of each other, within about 4 hours of each other, within about 1 hour of each other or within about 30 minutes of each other.

10-HDA, or a composition comprising 10-HDA, or a pharmaceutically acceptable salt thereof, in accordance with the invention may be administered by any route, including enteral (e.g., oral), parenteral, intravenous, intramuscular, intra-arterial, intramedullary, intrathecal, subcutaneous, intraventricular, transdermal, intradermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically, contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration). In particular embodiments, 10-HDA, or a composition comprising 10-HDA of the present invention are administered orally.

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

Where a carrier is used, the carrier must be pharmaceutically "acceptable" in the sense of being compatible with the other ingredients of the composition and not injurious to the subject. Compositions include those suitable for oral, rectal, nasal, topical (including buccal and sublingual), vaginal or parental (including subcutaneous, intramuscular, intravenous, and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

In some embodiments, where 10-HDA of the present invention is for oral administration, it may be prepared as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The 10-HDA may also be presented as a bolus, electuary or paste.

In some embodiments, where the 10-HDA is formulated as a tablet, the tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., inert diluent, preservative disintegrant (e.g., sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

In some embodiments, the 10-HDA, or compositions comprising 10-HDA, of the present invention may be in micro-encapsulated form with one or more excipients. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

In some embodiments, where the 10-HDA of the present invention is to be administered as a liquid dosage form for oral and parenteral administration, such a dosage form may include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the 10-HDA of the invention is mixed with solubilizing agents such as Cremophor™, alcohols, oils, modified oils, glycols, polysorbates, cyclodextrins, polymers, and mixtures thereof.

In some embodiments, where the 10-HDA, or a composition comprising 10-HDA, of the present invention is to be administered topically in the mouth, suitable dosage forms may include lozenges comprising the active ingredient in a flavoured base, usually sucrose and acacia or tragacanth gum; pastilles comprising the active ingredient in an inert basis such as gelatine and glycerin, or sucrose and acacia gum; and mouthwashes comprising the active ingredient in a suitable liquid carrier.

In some embodiments, where the 10-HDA, or composition comprising 10-HDA, of the present invention is to be administered topically to the skin, suitable dosage forms may include the dissolving or suspending the extract or component compound in any suitable carrier or base and may be in the form of lotions, gel, creams, pastes, ointments and the like. Suitable carriers include mineral oil, propylene glycol, polyoxyethylene, polyoxypropylene, emulsifying wax, sorbitanmonostearate, polysorbate 60, cetyl esters wax, cetearyl alcohol, 2-octyldodecanol, benzyl alcohol, and water. Transdermal patches may also be used to administer the extract or component compound of the invention.

In some embodiments, the 10-HDA, or composition comprising 10-HDA, of the present invention is for rectal administration, suitable dosage forms may include a suppository with a suitable base comprising, for example, cocoa butter, glycerin, gelatine or polyethylene glycol.

In some embodiments, where the 10-HDA, or composition comprising 10-HDA, of the present invention is for vaginal administration, suitable dosage forms may include pessaries, tampons, creams, gels, pastes, foams or spray formulations containing in addition to the active ingredient such carriers as are known in the art to be appropriate.

In some embodiments, where the 10-HDA, or composition comprising 10-HDA, of the present invention is for parenteral administration, suitable dosage forms may include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compound may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described. An injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In certain embodiments, unit dosage compositions are those containing a daily dose or unit, daily sub-dose, as herein above described, or an appropriate fraction thereof, of the active ingredient.

It should be understood that in addition to the active agent 10-HDA, compositions comprising 10-HDA of this invention may include other agents conventional in the art having regard to the type of composition in question, for example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include cornstarch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glycerylmonostearate or glyceryldistearate.

The phrase "pharmaceutically acceptable salt," as used herein, refers to pharmaceutically acceptable organic or inorganic salts of a provided compound. For use in medicine, the salts of the provided compounds will be pharmaceutically acceptable salts. Other salts may, however, be useful in the preparation of provided compounds or of their pharmaceutically acceptable salts. Pharmaceutically acceptable salts are well known in the art. For example, Berge et al., describe pharmaceutically acceptable salts in detail in *J. Pharm. Sci.* (1977) 66:1-19, incorporated herein by reference in its entirety. A pharmaceutically acceptable salt involves the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. When multiple charged atoms are present in the parent drug, its pharmaceutically acceptable salts will have multiple counter ions and these can be several instances of the same counter ion or different counter ions. Hence, a pharmaceutically acceptable salt can have one or more charged atoms in the parent compound and/or one or more counter ions.

Pharmaceutically acceptable salts of the compounds described herein include those derived from suitable inorganic and organic acids and bases. In some embodiments, the salts can be prepared in situ during the final isolation and purification of the compounds. In other embodiments the salts can be prepared from the free form of the compound in a separate synthetic step.

When a provided compound is acidic or contains a sufficiently acidic bioisostere, suitable "pharmaceutically acceptable salts" refers to salts prepared form pharmaceutically acceptable non-toxic bases including inorganic and organic bases. Salts derived from inorganic bases include aluminium, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N,N'-dibenzylethylenediamine, diethylamine, 2-di ethylaminoethanol, 2-dimethylaminoethanol, ethanolamine, ethylenediamine, N-ethylmorpholine, N-ethylpiperidine, glucamine, glucosamine, histidine, hydrab amine, isopropylamine, lysine, methylglucamine, morpholine, piperazine, piperidine, polyamine resins, procaine, purines, theobromine, triethylamine, trimethylaminetripropylamine, tromethamine and the like. Quarternary ammonium salts such as $N^+(C_{1-4}\ alkyl)_4$ are also included.

The preparation of the pharmaceutically acceptable salts described above and other typical pharmaceutically acceptable salts is more fully described by Berge et al., "Pharmaceutical Salts," *J. Pharm. Sci.,* 1977:66:1-19.

The formulations of 10-HDA, or compositions comprising 10-HDA, described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising 10-HDA and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

It will be appreciated that any compound that is a prodrug of 10-HDA, is also within the scope and spirit of the invention. The term "pro-drug" is used in its broadest sense and encompasses those derivatives that are converted in vivo to the compounds of the invention. Such derivatives would readily occur to those skilled in the art.

Furthermore, it is recognised that 10-HDA may be in crystalline form either as the free compound or as a solvate (e.g., hydrates) and it is intended that both forms are within the scope of the present invention. Methods of solvation are generally known within the art.

It is further recognised that in light of its structure, 10-HDA in accordance with the present invention may be capable of undergoing tautomerism. Accordingly, all possible tautomers of 10-HDA of the present invention fall within the scope and spirit of the invention.

As used herein, the term "derived from" shall be taken to indicate that a particular integer or group of integers has originated from the species specified, but has not necessarily been obtained directly from the specified source. For example, it is understood that 10-HDA may have originated from royal jelly, but has not necessarily been obtained directly from the specified source. Further, as used herein the singular forms of "a", "and" and "the" include plural referents unless the context clearly dictates otherwise.

Those skilled in the art will be aware that the invention described herein is subject to variations and modifications other than those specifically described. It is to be understood that the invention described herein includes all such variations and modifications. The invention also includes all such steps, features, methods, compositions and compounds referred to or indicated in this specification, individually or collectively, and any and all combinations of any two or more of said steps or features.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

Certain embodiments of the invention will now be described with reference to the following examples which are intended for the purpose of illustration only and are not intended to limit the scope of the generality hereinbefore described.

EXAMPLES

Example 1: In Vivo Mouse Models

Aromatase is expressed in high levels in the mouse medial amygdala and the same region is activated by interaction with a stranger mouse. In humans, aromatase is also highly expressed in the amygdala and fMRI studies suggest that the amygdala is less activated in people with OCD than controls. It was postulated that an Aromatase Knockout mouse (ArKO) model may exhibit behavioural phenotypes reflective of some of the key diagnostic behaviours and symptoms of OCD and anxiety disorder, including, for example OCD-like behavioural disturbances, such as repetitive behaviours.

Accordingly, an aromatase deficient mouse model (ArKO) was developed which presents the core OCD and anxiety disorder-like features, including social interaction deficit (FIGS. 1;A and B), compulsive wheel running (FIG. 2A to D) and compulsive grooming (FIG. 3C to F). The results described in FIG. 2 and FIG. 3 have been published at Hill et. al. Biol. Psychiatry (2007) 61:359-366.

Figure 1:
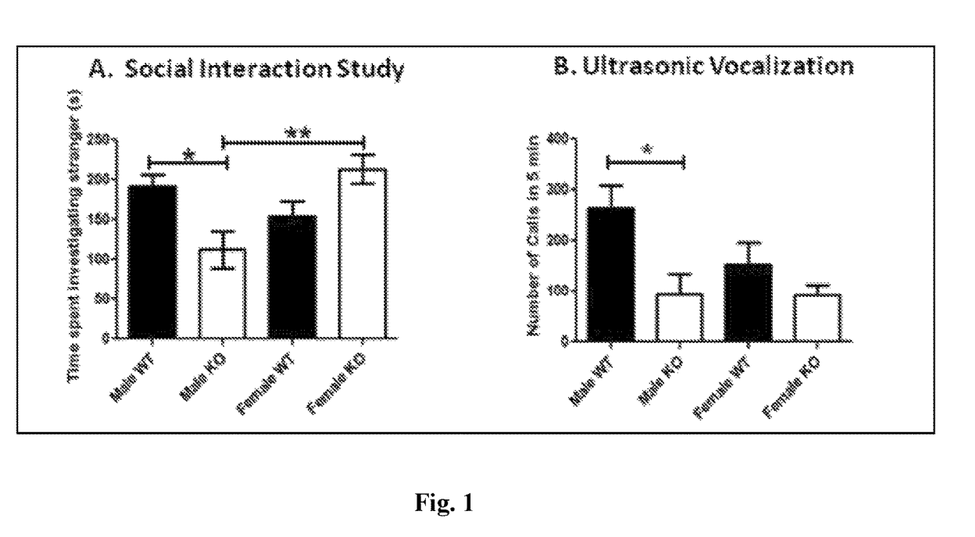
FIG. 1: Obsessive compulsive-like behaviour of aromatase knockout (ArKO) and wildtype (WT) mice; A. Social interaction study; B. Ultrasonic vocalization; wildtype (WT); ArKO mice (KO).
Figure 2:
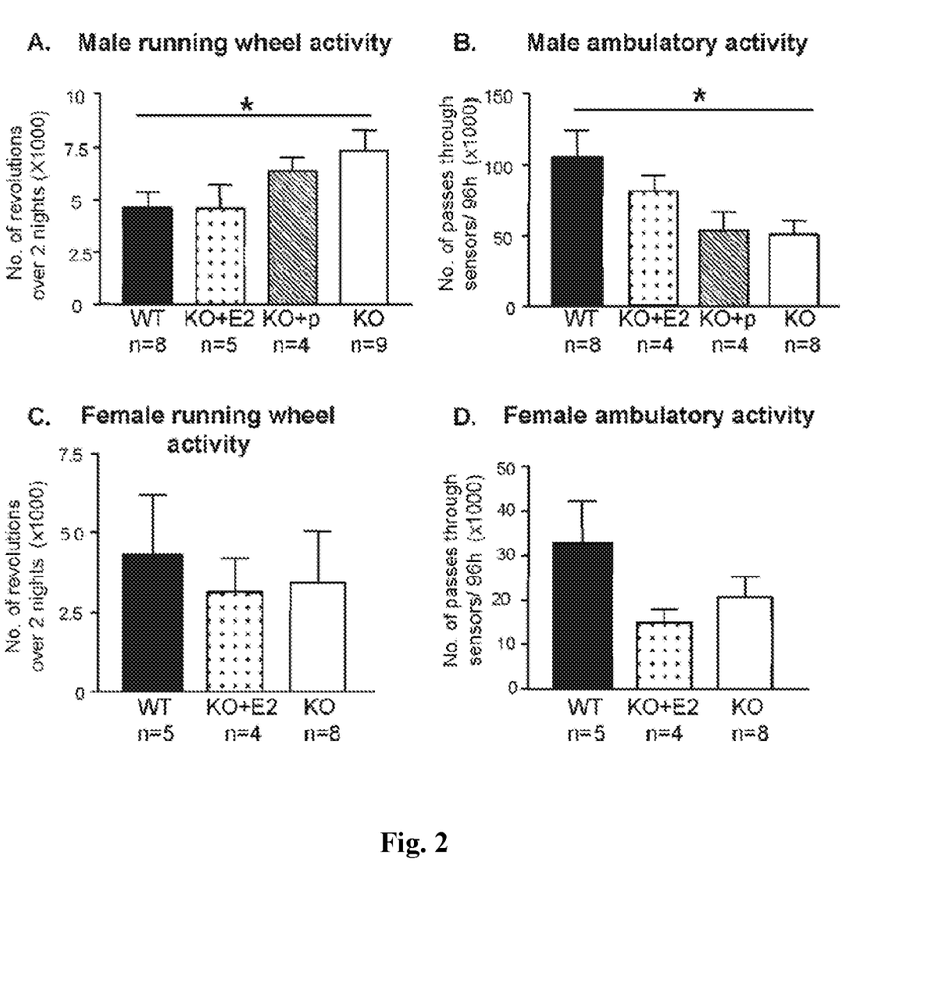
FIG. 2: Obsessive compulsive-like behaviour of aromatase knockout (ArKO) mice. A. Running wheel activity over two consecutive nights in 6-month old males. B. Ambulatory activity of 6-month old male animals over four days and four nights. C. Running wheel activity of 6-month old females. D. Ambulatory activity of 6-month old females; wildtype (WT), ArKO mice (KO), 17 β-estradiol treated ArKO mice (KO+E2), placebo treated ArKO mice (KO+p).
Figure 3:
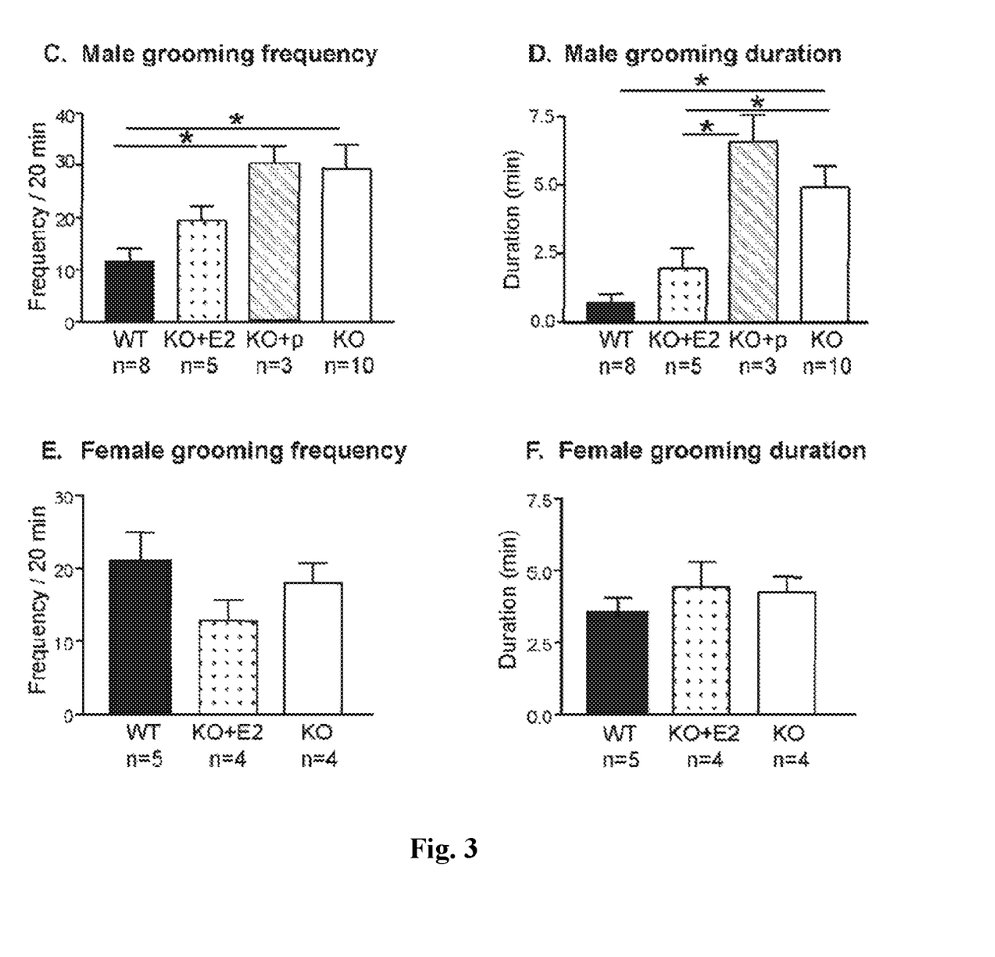
FIG. 3: Obsessive compulsive-like behaviour of aromatase knockout (ArKO) mice; C. Frequency of initiation of grooming of male animals over a 20-min period post water mist spray. D. Duration of grooming of male animals over 20-min time period post water mist spray. E. Frequency of initiation of grooming of 6 month-old female animals during a 20-min period post water mist spray. F. Duration of grooming of 6 month-old female animals over a 20-min period post water mist spray; wildtype (WT), ArKO mice (KO), estradiol treated ArKO mice (KO+E2), placebo treated ArKO mice (KO+p).

Specifically, the inventors have found that the lack of a normal functioning aromatase will precipitate the following OCD-like behavioural disturbances in the male ArKO (aromatase knockout) mouse, but not in the female ArKO mouse:

i) Abnormal Social interaction (FIG. 1A): Juvenile (4 week-old) male ArKO mice were found to spend significantly less time investigating the stranger mouse than wild-type male mouse (WT). Conversely, the female ArKO and WT mice were found to spend similar amounts of time with the stranger mouse.

ii) Ultrasonic vocalization deficit (FIG. 1B): Male ArKO 9-day old pups were found to vocalise significantly less than male WT litter mates when separated from their litters iii) Compulsive wheel-running: Male ArKO mice were also found to spend significantly more time on the running wheel when compared with WT and female ArKO mice (FIG. 2).

iv) Compulsive grooming: Male ArKO mice were found to groom more frequently (FIG. 3C) and for longer periods of time (FIG. 3D), when compared with WT and female ArKO mice. Specifically, the grooming activity of each animal was analysed for 20 min after administration of water mist spray (a trigger for grooming). Male ArKO mice exhibited significantly ($p<0.05$) heightened grooming activity in terms of frequency of initiation and duration of grooming. Compulsive grooming observed in ArKO represents an OCD-like repetitive behavioural disturbance in OCD-patients.

Example 2: In Vivo Mouse Model Treated with 10-HDA

Figure 4:
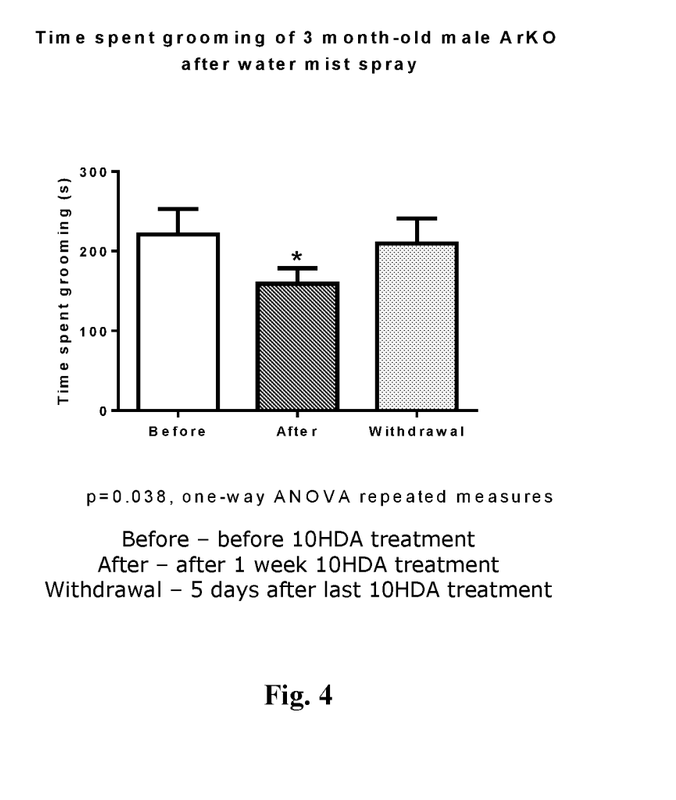
FIG. 4: Treatment of aromatase knockout (ArKO) mice with 10-HDA; duration of of grooming of male animals over a 10-min period post-water mist spray; before treatment with 10-HDA and after treatment with 10-HDA.

ArKO mice exhibiting behavioural phenotypes reflective of some of the key diagnostic behaviours and symptoms of OCD and anxiety disorder, including repetitive behaviours such as compulsive grooming, were administered 10-HDA (FIG. 4). Specifically, male 3 month-old ArKO mice (n=5) were injected daily with 10-HDA (500 µg/kg) for 1 week. Similarly to Example 1 (see above), water mist spray triggered grooming was assessed before and after administration of 10-HDA treatment. During grooming assessment, each mouse was subjected to two squirts of sterile water mist spray and its grooming activity was recorded for 10 min immediately after the mist spray. Grooming duration was analyzed statistically by paired t test. A significant reduction in duration of grooming was observed after administration of 10-HDA to the ArKO mice (p=0.0363). Further grooming assessment was performed 5 days after the last administration of 10-HDA. After the withdrawal period grooming duration was found to return to pre-treatment levels (FIG. 4).

Example 3: Next Generation Sequencing of Primary Cortical Neurons Harvested from Mice Foetal cortices of C57Black 6 mice (gestational days 15) were micro-dissected and subjected to trypsin digestion and mechanical trituration and centrifugation. The pelleted cells were resuspended in Neurobasal™ medium (NBM) containing 2.5% B-27 supplement, 1% penicillin, 1% streptomycin, 0.25% GlutaMAX-1 supplement and 10% dialysed foetal calf serum. Cells were seeded on poly-d-lysine (100 µg/ml) coated 12-well plates to a density of $400 \times 10^5$ cells/cm$^2$. Cultures were maintained at 37° C. in a humidified 5% $CO_2$ and 95% air incubator and were subsequently cultured after day 1 in serum-free medium. After 24 hours, primary cortical neurons were treated with DMSO or 1 mM 10-HDA, and harvested for total RNA preparation on Day 7 for subsequent Next Generation Sequencing (RNAseq). There were 4 biological repeats, i.e. 4 individual dams; 4 technical repeats per biological repeat, i.e. 4 plates per individual mouse and 3 wells per treatment.

Samples were kept cold during the harvesting of cortical neurons for RNA preparation. Culture medium was removed by aspiration, and 100 µL of ice-cold Cell Disruption Buffer (Paris Kit, Ambion®) added per well. i.e. 300 µL for $\geq 10^6$ cells. The cells were lysed immediately upon exposure to the Cell Disruption Buffer; wells were scraped with wide end of 200 µl RNA free pipette tip and lysates were then transferred into a 1.7 ml Eppendorf tube. To completely lyse the cells, the lysate was pipetted vigorously till a homogenous lysate was obtained. All lysates were stored at −80° C.

Total RNA was extracted from each sample using the PARIS kit (Ambion). The quality of RNA was assessed by LabChip® (Perkin Elmer). Libraries were generated from the total RNA using SureSelect Strand Specific RNA Library Prep for Illumina Multiplexed Sequencing (Agilent Technologies). The libraries were sequenced with 50 bp single end reads using Illumina Hiseq and subjected to bioinformatic analyses. Sequencing data were assessed (FastQC) and aligned to mouse genome using Subjunc aligner within the Subread package. Sequencing data was summarised into Reads per transcript using Feature counts and the Gencode gene models for the mouse genome build. Normalisation and statistical analysis on the count data was performed using EdgeR and scaled using trimmed mean of M-values (TMM).

Figure 5:
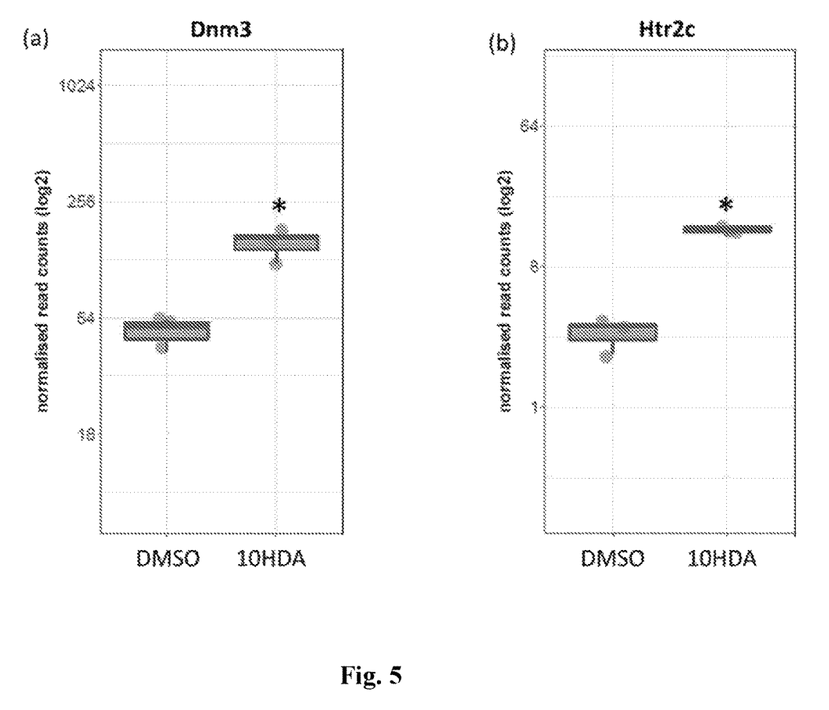
FIG. 5: Box plots of expression levels of (a) dynamin 3 and (b) 5-hydroxytryptamine (serotonin) receptor 2C transcripts in primary cortical cultures with vehicle or 10-HDA treatments as determined by Next Generation Sequencing.

Next Generation Sequencing data showed that 10-HDA significantly upregulated transcript expression levels of dynamin 3 and 5-hydroxytryptamine (serotonin) receptor 2C (FIG. 5). Both genes are implicated in Obsessive Compulsive Disorders (*Transl. Psychiatry.* 2016 Mar. 29; 6:e768, *Eur. Neuropsychopharmacol.* 2000 May 10(3): 205-8, *Expert Opin Investig Drugs.* 1998 October; 7(10):1587-99, *Physiol. Behav.* 2003 April; 78(4-5):641-9).

What is claimed is:

1. A method for the treatment of a repetitive behavioral pattern in a subject having obsessive compulsive disorder, comprising administering to a mammal in need thereof an effective amount of 10-hydroxy-2-decenoic acid or a pharmaceutically acceptable salt thereof.

2. The method of claim 1, comprising administering an effective amount of trans 10-hydroxy-2-decenoic acid or a pharmaceutically acceptable salt thereof.

3. The method of claim 1, comprising administering an effective amount of cis 10-hydroxy-2-decenoic acid or a pharmaceutically acceptable salt thereof.

4. The method of claim 1, comprising administering an effective amount of a racemic mixture of trans and cis 10-hydroxy-2-decenoic acid or a pharmaceutically acceptable salts thereof.

5. The method of claim 1, wherein the 10-hydroxy-2-decenoic acid or a pharmaceutically acceptable salt thereof is administered as a composition.

6. The method of claim 5, wherein the composition comprises royal jelly, an extract of royal jelly, or a composition derived from royal jelly.

7. The method of claim 1, wherein the effective amount of 10-hydroxy-2-decenoic acid or a pharmaceutically acceptable salt thereof is in the range of 0.01 to 6000 mg/day, 0.1 to 5000 mg/day, 1 to 4000 mg/day, 10 to 3000 mg/day, 100 to 2000 mg/day, or 500 to 1500 mg/day.

8. The method of claim 1, wherein the effective amount of 10-hydroxy-2-decenoic acid or a pharmaceutically acceptable salt thereof is selected from the group consisting of 0.5 mg/day, 1 mg/day, 5 mg/day, 10 mg/day, 50 mg/day, 100 mg/day, 250 mg/day, 500 mg/day, 750 mg/day, 1000 mg/day, 1500 mg/day and 2000 mg/day.

9. The method of claim 1, wherein the mammal is a human.

* * * * *